United States Patent
Snow (10) Patent No.: US 6,186,985 B1
(45) Date of Patent: Feb. 13, 2001

(54) GASTRO-INTESTINAL TUBE WITH DISSOLVABLE SUPPORT BOLSTER

(75) Inventor: Todd Snow, Westboro, MA (US)

(73) Assignee: Boston Scientific Corporation, Natick, MA (US)

(*) Notice: Under 35 U.S.C. 154(b), the term of this patent shall be extended for 0 days.

(21) Appl. No.: 08/943,918

(22) Filed: Oct. 3, 1997

(51) Int. Cl.$^7$ .................................................. A61M 5/32
(52) U.S. Cl. ........................................... 604/175; 604/264
(58) Field of Search .................................. 604/264, 265, 604/270, 174, 175

(56) References Cited

U.S. PATENT DOCUMENTS

| | | | |
|---|---|---|---|
| 4,315,513 | * 2/1982 | Nawash et al. | 128/348 |
| 4,649,913 | * 3/1987 | Watson | 604/174 |
| 4,702,917 | * 10/1987 | Schindler | 604/890 |
| 4,863,438 | 9/1989 | Gauderer et al. | |
| 5,007,900 | 4/1991 | Picha et al. | |
| 5,041,100 | * 8/1991 | Rowland et al. | 604/265 |
| 5,085,629 | 2/1992 | Goldberg et al. | |
| 5,234,457 | 8/1993 | Andersen. | |
| 5,248,302 | 9/1993 | Patrick et al. | |
| 5,267,968 | * 12/1993 | Russo | 604/174 |
| 5,279,564 | 1/1994 | Taylor. | |
| 5,321,113 | * 6/1994 | Cooper et al. | 528/176 |
| 5,342,628 | 8/1994 | Picha. | |
| 5,356,391 | 10/1994 | Stewart. | |
| 5,366,504 | 11/1994 | Andersen et al. | |
| 5,366,505 | 11/1994 | Faber. | |
| 5,391,159 | 2/1995 | Hirsch et al. | |
| 5,445,615 | * 8/1995 | Yoon | 604/174 |
| 5,464,450 | 11/1995 | Buscemi et al. | |
| 5,531,716 | 7/1996 | Luzio et al. | |

FOREIGN PATENT DOCUMENTS

| | | |
|---|---|---|
| 0 183 372 | 6/1986 | (EP). |
| 0 420 541 A2 | 4/1991 | (EP). |
| 2127839 | 4/1984 | (GB). |

OTHER PUBLICATIONS

"Prevention of Bacterial Colonization on Polyurethane in vitro by incorporated antibacterial agent", Journal of Biomedical Materials Research, vol. 25, 937–952 (1991).

* cited by examiner

*Primary Examiner*—Sharon Kennedy
*Assistant Examiner*—Deborah Blyveis
(74) *Attorney, Agent, or Firm*—Kenyon & Kenyon (57) ABSTRACT

A gastro-intestinal tube which provides rigid support during stomal formation, while allowing tube removal by pulling from outside the abdominal wall. The tube has proximal and distal ends, a deformable internal bolster attached to the distal end, and a dissolvable support bolster placed around the tube proximal to the internal bolster. The support bolster is made of a dissolvable material, such that the bolster provides a high degree of securement to the gastro-intestinal tube during formation of the stoma, and dissolves to allow tube removal after the stoma has formed. In an alternate embodiment, the bolster has a coating of a medicating agent.

33 Claims, 6 Drawing Sheets

GASTRO-INTESTINAL TUBE WITH DISSOLVABLE SUPPORT BOLSTER

FIELD OF THE INVENTION

The present invention relates generally to an apparatus for use in the placement of gastro-intestinal devices. More specifically, the present invention relates to a gastro-intestinal device having a deformable internal bolster and a dissolvable support bolster.

BACKGROUND OF THE INVENTION

Medical practitioners utilize a variety of gastro-intestinal devices to access the gastro-intestinal tract. One type of gastro-intestinal device, the gastro-intestinal tube, is widely used with patients who require catheterization for the purposes of, for example, delivering food or medication to the gastro-intestinal tract, draining the tract, or creating a surgical port. Patients with damage to their upper gastro-intestinal tract, or with neurological or mental impairment often need long-term catheterization for these purposes. In order to place catheters within the gastro-intestinal tract, medical practitioners often use Percutaneous Endoscopic Gastrostomy (PEG) techniques. These techniques typically involve either placing a gastro-intestinal tube in the patient's mouth and snaking it down the esophagus, into the stomach, and out the abdominal wall, or they involve inserting the tube into the stomach from outside of the abdominal wall by sliding the tube over a guidewire.

Gastro-intestinal tubes, like other gastro-intestinal devices which provide access to the gastro-intestinal tract, typically have an internal bolster, or anchoring device, at one end which secures the tube within the stomach. When the tube is properly placed, the end having the bolster lies inside the stomach wall. The tube is pulled from outside the abdomen until the internal bolster forces the stomach against the abdominal wall; a process called "approximation." An additional bolster is often placed on the outside of the abdominal wall to hold the stomach in contact with the abdominal wall. After the stomach and abdominal wall are held in place for approximately two weeks, a fistulous tract, called a stoma, forms which runs from the stomach to the outer surface of the abdominal wall.

When using percutaneous gastrostomy, practitioners face several common complications, including: infection at the stoma site, premature tube removal, and tube migration. Peristomal infections, the most common post-placement complication, result from introducing a gastro-intestinal tube into the sterile abdominal penetration, after the tube has been dragged through non-sterile locations such as the mouth, esophagus, and the external abdominal wall. Although prophylactic medication often prevents infection, peristomal infection still occurs in a small percentage of cases where prophylactic treatment has been administered.

Most gastro-intestinal tubes used in long-term catheterization remain in place for several months. During that time, the tubes are manipulated by medical practitioners who clean the stoma site, attach and detach devices for delivering food and medicine, and otherwise move the tubes. The tubes are also manipulated by patients, some of whom suffer from mental or neurological disorders and try to remove the tube by pulling it from outside the abdominal wall. Such manipulation can cause the tube to become misplaced within or removed from the gastro-intestinal tract.

If the tube is deliberately or inadvertently pulled before the stoma forms, it may fall out of the stomach wall and become misplaced either within the abdominal wall or within the peritoneal cavity which is sterile and susceptible to infection. Since peritoneal infection often goes unnoticed until it has become severe, misplacing the tube within that cavity can cause serious medical complications. If the tube is pulled after the stoma has formed, it may be completely removed from the stoma, requiring replacement procedures. The internal bolster may also rupture the stomal tract as it is pulled through, requiring subsequent medical procedures.

Tube migration refers to post-placement tube movement within the stomach and abdominal walls. Migration typically results from clamping the outer bolster too tightly against the abdomen during approximation. Excessive clamping pins the internal bolster tightly against the stomach wall, often leading to ulceration and necrosis of the gastric tissue. As the tissue dies or is displaced, the bolster migrates into the body tissue. Because PEG approximation is usually performed without endoscopic visualization, the excessive clamping often goes undetected.

If migration occurs before the stomal tract forms, the bolster may become misplaced within the peritoneal cavity. Migration into the peritoneal cavity often leads to severe infection and, where the tube is used for feeding or medication delivery, to misdirected delivery into the peritoneal cavity. Tube migration often goes undetected until observable manifestations, such as bleeding, occurs.

A high incidence of tube migration occurs where flexible internal bolsters are used. Although such bolsters enable tube removal by pulling the tube from outside the abdominal wall, they are also more susceptible to tube migration. When outer bolsters are used in connection with flexible internal bolsters and clamped tightly, the flexible internal bolster may be pulled into the abdominal penetration. Due to their flexible structure of these flexible bolsters, they often migrate further into the penetration.

Another common complication from using percutaneous gastrostomy relates to deliberate tube removal by medical personnel. Gastro-intestinal tubes often become occluded or clogged and must be removed and replaced. They are also periodically removed and replaced during normal medical maintenance. Some tubes have rigid internal bolsters which prevent removal by pulling from outside the abdominal wall. These bolsters must be removed either surgically or by endoscopic snare. Other tubes have internal bolsters which detach when the tube is traction pulled, and are left to be expelled from the body through excretion. These additional invasive procedures increase patient discomfort, risk of infection, as well as medical expenses.

Applied Medical Technologies, Inc. of Independence, Ohio markets a device called the "Secure Cath Adaptor" having a rigid disk which fits over the tube shaft, up against a more flexible internal bolster. The rigid disk is designed to prevent removal by pulling the tube from outside the abdominal wall; called removal by traction pull or traction removal. Thus, in addition to preventing premature traction removal, the disk prevents traction removal for tube replacement. The "Secure Cath Adapter" tube must then be removed by using an endoscopic snare, an invasive and often expensive medical procedure. Practitioners may nevertheless attempt traction removal, as such removal is often performed without internal visualization. In the process, the stomal tract may be damaged.

The prior art contains several gastro-intestinal tubes which inhibit premature removal to some degree while allowing deliberate removal by medical personnel. U.S. Pat. No. 5,356,391 describes a tube with a collapsible internal bolster. During normal operation, the bolster retains its domed shape. During traction pull, the dome collapses to a diameter which allows the bolster to pass through the stoma. A similar device is described in U.S. Pat. No. 5,391,159. U.S. Pat. No. 5,248,302 describes an internal bolster which can be removed through use of an obturator.

SUMMARY OF THE INVENTION

The present invention overcomes the deficiencies in the prior art by providing a gastro-intestinal device which prevents premature traction removal, but allows certain deliberate traction removal, such as removal for purposes of replacement. The invention comprises a gastro-intestinal tube with a deformable internal bolster located at the distal end. The invention further comprises a dissolvable support bolster which is located proximally adjacent to the internal bolster. The support bolster provides rigid support to the internal bolster prior to dissolution of the support bolster and thereby preventing premature tube removal. After the support bolster dissolves, however, the tube can be removed by traction pulling the tube through the penetration into which it had been placed.

In the preferred embodiment, the dissolution time of the support bolster is such that the support bolster provides rigid support during formation of a fistulous tract connecting the stomach to the abdominal wall, called a stoma. The stoma typically takes approximately two weeks from initial tube placement to form. If the tube is inadvertently or deliberately pulled before stoma formation, the internal bolster may be pulled into and become misplaced within the peritoneal cavity, and the stomach may then fall away from the abdominal wall. Should that occur, a second surgical procedure would likely be required to place another gastro-intestinal tube.

In another embodiment, the support bolster has a coating which contains a substance such as an anti-inflammatory, antibiotic, antiviral, antiencrustation, antimicrobial, or disinfecting agent. Additionally, the shaft of the gastro-intestinal tube can be coated with such a substance.

BRIEF DESCRIPTION OF THE DRAWINGS

The invention will be more readily understood through the following detailed description, with reference to the accompanying drawings, in which:

FIG. 8b is an end view of the gastro-intestinal tube having a dissolvable support bolster shown in FIG. 8a.

FIG. 9b is an end view of the gastro-intestinal tube having a dissolvable support bolster shown in FIG. 9a.

FIG. 10b is an end view of the gastro-intestinal tube having a dissolvable support bolster shown in FIG. 10a.

FIG. 11b is an end view of the gastro-intestinal tube having a dissolvable support bolster shown in FIG. 11a.

FIG. 12b is an end view of the gastro-intestinal tube having a dissolvable support bolster shown in FIG. 12a.

FIG. 13b is an end view of the gastro-intestinal tube having a dissolvable support bolster shown in FIG. 13a.

FIG. 14b is an end view of the gastro-intestinal tube having a dissolvable support bolster shown in FIG. 14a.

FIG. 15b is an end view of the gastro-intestinal tube having a dissolvable support bolster shown in FIG. 15a.

FIG. 16b is an end view of the gastro-intestinal tube having a dissolvable support bolster shown in FIG. 16a.

FIG. 17b is an end view of the gastro-intestinal tube having a dissolvable support bolster shown in FIG. 17a.

FIG. 18b is an end view of the gastro-intestinal tube having a dissolvable support bolster shown in FIG. 18a.

FIG. 19b is an end view of the gastro-intestinal tube having a dissolvable support bolster shown in FIG. 19a.

DETAILED DESCRIPTION OF THE INVENTION

Figure 1:
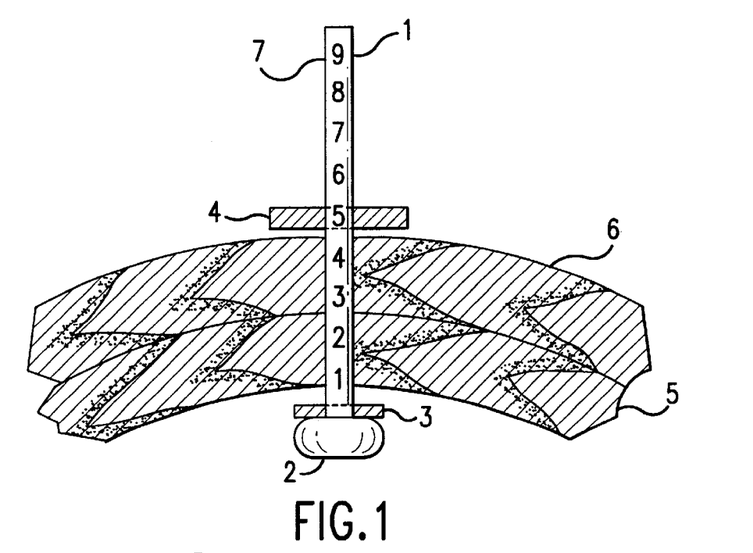
FIG. 1 shows an elevational view, partially in section, of a gastro-intestinal tube constructed according to the principles of this invention, as placed within the gastric cavity.

The preferred embodiment of the present invention comprises a gastro-intestinal tube 1 having proximal and distal ends, an internal bolster 2 attached to the distal end, a dissolvable support bolster 3 which is located proximally adjacent to the internal bolster. FIG. 1 shows a dissolvable support bolster which is placed around the tube shaft 7 of the tube 1, just proximal to the internal bolster 2. FIG. 1 also shows an external bolster 4 placed around the tube shaft 7 just proximal to the abdominal wall 6.

FIG. 1 shows an elevational view of the preferred embodiment as properly placed within the body. The gastro-intestinal tube 1 can be placed either transorally or percutaneously, using any of the methods for placing gastro-intestinal devices known in the prior art. For example, the tube may be placed using either the push or pull PEG techniques known in the art. When properly placed, the dissolvable bolster 3 is adjacent to the inner gastric wall 5, proximal to the internal bolster 2. The tube 1 extends from inside the gastric wall 5 out through the external abdominal wall 6.

Figure 2:
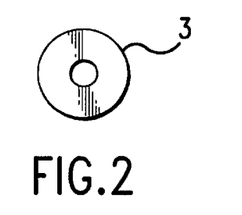
FIG. 2 is a top view of an embodiment of dissolvable support bolster of the present invention, where the support bolster is shaped as a disk.
Figure 3:
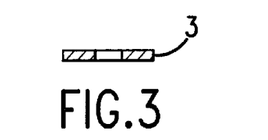
FIG. 3 is a side view of the dissolvable support bolster shown in FIG. 2.

FIGS. 2 and 3 show the support bolster 3 of the present invention. The support bolster 3 is preferably a round disk with an outer diameter of approximately 2–3 cm, and an inner diameter sized to allow fitting the disk around the outer diameter of the tube shaft 7, which, for gastro-intestinal tubes, is typically between 14 fr. and 28 fr.(i.e 4.55 mm and 8.9 mm). Although the thickness of the support bolster 3 can vary, in the preferred embodiment, the support bolster is a disk with a thickness of 2–3 mm. Generally, the support bolster need only have a size and thickness sufficient to prevent premature tube removal.

Further, the dissolvable support bolster 3 need only be as rigid as necessary to prevent premature removal through the penetration that eventually forms the stoma tract. The support bolster 3 can be pliant enough to allow compression or manipulation during tube insertion, yet still rigid enough to prevent premature removal.

The support bolster 3 is made of a dissolvable biocompatible material, preferably an aliphatic polyester, such as the material used to make medical suture. However, the support bolster 3 can also be made of any biocompatible, dissolvable material known in the art, such as dissolvable polymers or other materials (e.g. collagen, elastin, chitin). Examples of dissolvable polymers include poly [phosphoesters], poly[anhydrides], poly[orthoesters], poly [phosphazenes], poly[anhydrides], polysaccharides, peptide-based polymers, and poly[α-esters]. In addition, U.S. Pat. No. 5,035,629 (incorporated herein by reference for this purpose) describes several compositions used to form biocompatible, dissolvable medical devices.

The dissolution time for the support bolster is preferably between two and four weeks, which is the amount of time a stomal tract typically takes to form. This allows the support bolster 3 to rigidly support the internal bolster during stomal formation, yet permit traction removal of the tube 1 shortly thereafter. However, the dissolution time can be shorter than two weeks or longer than four weeks, and techniques for varying the dissolution time of biocompatible compounds are well-known in the art. Since gastro-intestinal tubes typically remain in vivo for less than six months, the dissolution time of the support bolster 3 will not usually be longer than six months.

The gastro-intestinal tube shaft 7 can be made of any biocompatible copolymer such as a silicone elastomer, silicone copolymer or polyurethane. The use of copolymers to form the shaft of a gastro-intestinal tube is well-known in the art.

The internal bolster 2 is made of a collapsible material such that, after the support bolster 3 dissolves, the tube can be removed by traction pulling from outside the abdominal wall 6. Several materials and structures for collapsible internal bolsters exist in the prior art. Examples can be found in U.S. Pat. No. 5,356,391 and U.S. Pat. No. 5,391,159 (the contents of these patents are incorporated herein by reference for these teachings). Another example is the internal bolster used with the device marketed as the "Secure Cath Adapter" by Applied Medical Technologies.

Figure 4A:
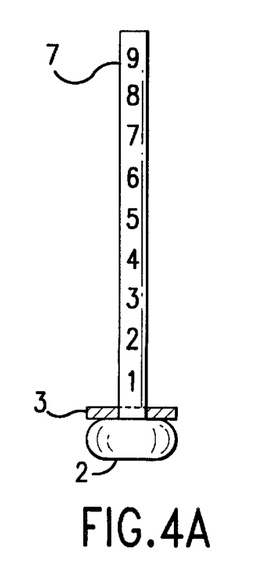
FIG. 4a is an elevational view, partially in section, of an embodiment of gastro-intestinal tube having a dissolvable support bolster constructed according to the principles of this invention.
Figure 4B:
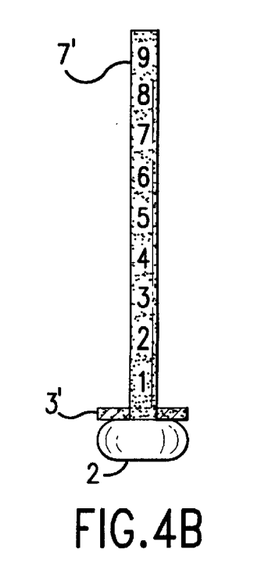
FIG. 4b is an elevational view, partially in section, of the embodiment of gastro-intestinal tube having a dissolvable support bolster shown in FIG. 4a, with both the tube shaft and dissolvable support bolster coated with a substance.

In another embodiment of the present invention, shown in FIG. 4b, the outer surface of the support bolster 3' has a coating which contains a medicating substance. When a gastro-intestinal tube having such a support bolster 3' is placed within the abdominal cavity, the support bolster 3' lies distally adjacent to the gastric wall, as shown in FIG. 1. The coating of the support bolster 3' enables delivery of the medicating substance from the support bolster 3' directly to the gastric wall, where infection and inflammation is most likely to occur. Typically, the coating will include an anti-inflammatory drug, such as salicylic acid or prednisone. The coating may also include an antibiotic, antiviral, antimicrobial, or antiencrustation agent, or a disinfecting agent such as a bacteriocidal or bacteriostatic agent. Ciprofloxacin or gentamicin are examples of antibiotics which can be used with this embodiment. Chlorhexadine and triclosan are examples of disinfecting agents which can be used. U.S. Pat. No. 5,366,505 describes the use of slime-inhibiting compounds in connection with medical devices to inhibit the growth of microorganisms thereon (the contents of this patent are incorporated herein by reference for these teachings). Such compounds may be used with the present invention.

As an alternative to coating the support bolster with a medicating substance, such a substance may be located, placed, or formed within the dissolvable support bolster 3'. Dissolvable materials make good drug delivery agents, avoiding the need for a coating which includes a medicating substance. The use of biocompatible, dissolvable devices for medication delivery is well known in the art. Typically, the device is made with a porous structure. The medication is then loaded into the pores of the device, which is placed within the body. This method of dispensing medication is described in U.S. Pat. No. 4,702,917. U.S. Pat. Nos. 3,887, 699 and 4,148,871 also describe biocompatible materials used to dispense medication (the contents of these patents are incorporated herein by reference for these teachings). U.S. Pat. Nos. 5,234,457 and 5,464,450 also describe the use of dissolvable materials for medication delivery (the contents of these patents are incorporated herein by reference for these teachings). Examples of biocompatible, dissolvable materials which can be coated with medication include: aliphatic polyesters (such as DECAPEPTYL LUPRON DEPOT, ZOLADEX and ATRIGEL), poly[phosophesters], poly[anhydrides], poly[α-esters], and polyalphahydroxy acids.

The rates at which the support bolster dissolves and the medication is dispensed can be controlled with the use of a rate-limiting membrane with the support bolster. The use of such a membrane is known in the art. See Golomb et al, Journal of Biomedical Materials Research, 25(8), 1991, 937–952.

Additionally, the shaft 7' of the gastro-intestinal tube may contain a medicating agent, as shown in FIG. 4b. Medication, so located, can be delivered directly to the tissue of the penetration which forms the stoma tract, thereby alleviating the risk of infection, inflammation, or encrustation within that tract. For example, a distal portion of the tube shaft 7, 9 cm. in length, can be coated or otherwise equipped with a antibiotic or anti-inflammatory medication. (FIG. 4a shows a gastro-intestinal tube of the present invention in which neither the shaft 7 of the tube nor the support bolster 3 have a medicating substance coating.)

Medication may also be located on or within the internal bolster 2, in a manner described above. The degree to which the internal bolster 2 is in direct contact with the gastric wall depends largely on the size and configuration of the support bolster 3. Where portions of the internal bolster 2 are in direct contact with the gastric wall, medication located on that bolster can be delivered directly. Even where the internal bolster 2 is not in direct contact, however, medication located on or within the internal bolster 2 can be released into the gastric lumen. In addition, as the support bolster 3 dissolves, a greater portion of the internal bolster 2 may come into direct contact with the gastric wall.

U.S. Pat. No. 5,366,504 describes a tubular prosthesis having a drug incorporated within a dissolvable coating. The contents of that patent are incorporated herein for those teachings.

Figure 5A:
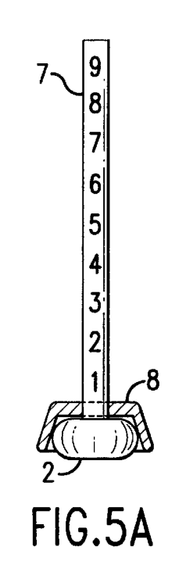
FIG. 5a is an elevational view, partially in section, of an embodiment of gastro-intestinal tube having a dissolvable support bolster constructed according to the principles of the present invention.
Figure 5B:
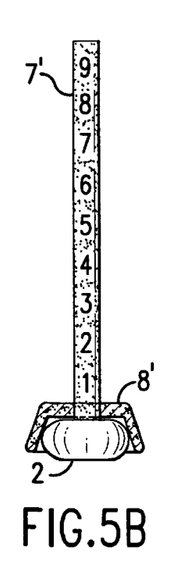
FIG. 5b is an elevational view, partially in section, of the embodiment of gastro-intestinal tube having a dissolvable support bolster shown in FIG. 5a, with both the tube shaft and support bolster coated with a substance.
Figure 6A:
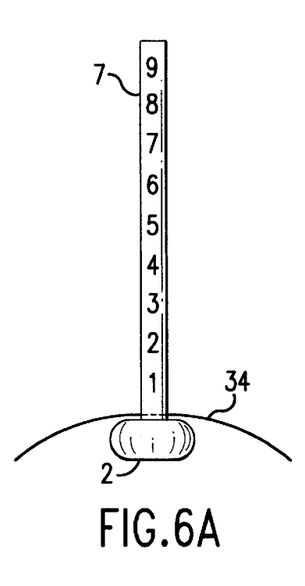
FIG. 6a is an elevational view, partially in section, of a gastro-intestinal tube with a dissolvable support bolster having an extended lateral extent, constructed according to the present invention, as placed within the gastric cavity.
Figure 6B:
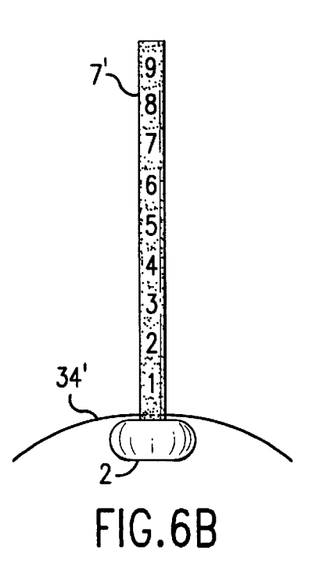
FIG. 6b is an elevational view, partially in section, of the embodiment of gastro-intestinal tube with dissolvable support bolster having an extended lateral extent, with both the tube shaft and the dissolvable support bolster coated with a substance according to the principles of the present invention.
Figure 7A:
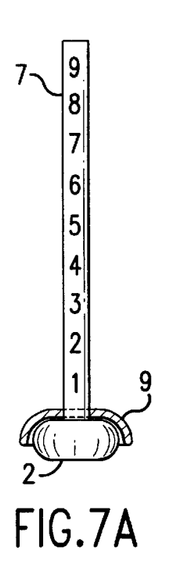
FIG. 7a is an elevational view, partially in section, of an embodiment of gastro-intestinal tube having a dissolvable support bolster constructed according to the principles of the present invention.
Figure 7B:
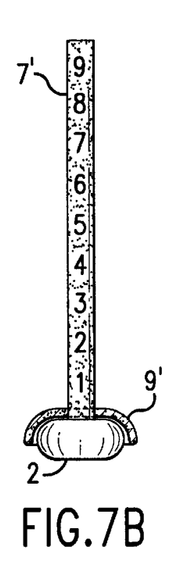
FIG. 7b is an elevational view, partially in section, of the embodiment of gastro-intestinal tube having a dissolvable support bolster shown in FIG. 7a, with both the tube shaft and dissolvable support bolster coated with a substance according to the present invention.

FIG. 4a shows a gastro-intestinal tube of present invention with a internal bolster 2 having a flattened bulbous shape. That figure also shows a support bolster 3 shaped as disk. However, these bolsters can vary widely in shape. FIGS. 5a and 7a show gastro-intestinal tubes of the present invention with support bolsters 8 and 9, respectively, which are formed to partially surround the internal bolster 2. FIG. 6a shows a support bolster 34 with an extended lateral extent. Each of the support bolsters depicted in FIGS. 5a, 6a, and 7a provide a greater surface area than that provided by the support bolster 3, shown in FIG. 4. With this increased surface area, a medicating substance can be delivered directly to a larger area of the gastric wall. (FIGS. 5b, 6b, and 7b show gastro-intestinal tubes of the present invention in which both the support bolster and tube shaft are equipped with a medicating substance).

Figure 8A:
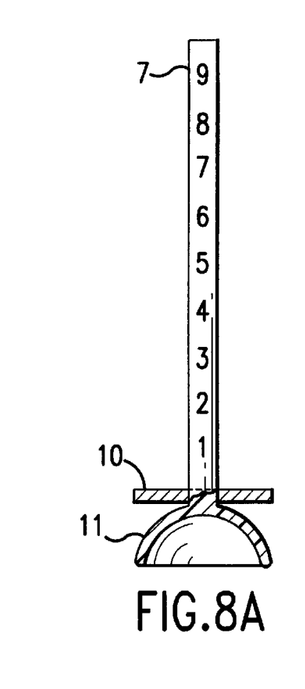
FIG. 8a is an elevational view, partially in section, of an embodiment of gastro-intestinal tube having a dissolvable support bolster constructed according to the principles of the present invention, in which the internal bolster is convex, as viewed from a proximal vantage point, and oval in shape, as viewed from an end.
Figure 8B:
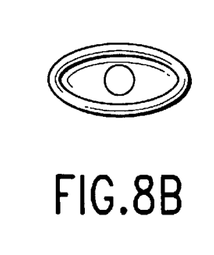

It is within the scope of the invention to use a variety of shapes for the internal bolster and the support bolster, as variations in shape can affect, among other things, the ease with which the gastro-intestinal device can be placed or removed, and the area of the gastric wall to which a substance can be directly delivered. For example, the embodiment illustrated in FIG. 8a shows a gastro-intestinal tube of the present invention in which the internal bolster 11 is proximally convex and oval in shape (as viewed from an end). The convex shape of the internal bolster 11 facilitates traction removal of the tube once the support bolster 10 has dissolved. FIG. 8b is an end view of the gastro-intestinal tube shown in FIG. 8a.

Figure 9A:
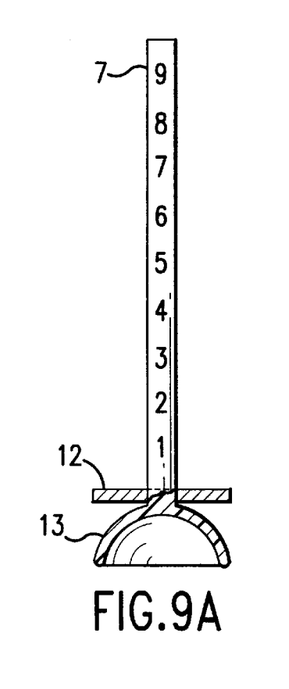
FIG. 9a is an elevational view, partially in section, of an embodiment of gastro-intestinal tube having a dissolvable support bolster according to the present invention, in which the internal bolster is convex, as viewed from a proximal vantage point, and circular in shape, as viewed from an end.
Figure 9B:
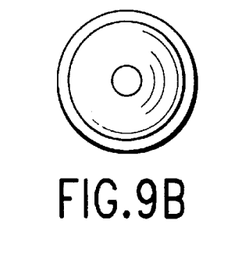
Figure 10A:
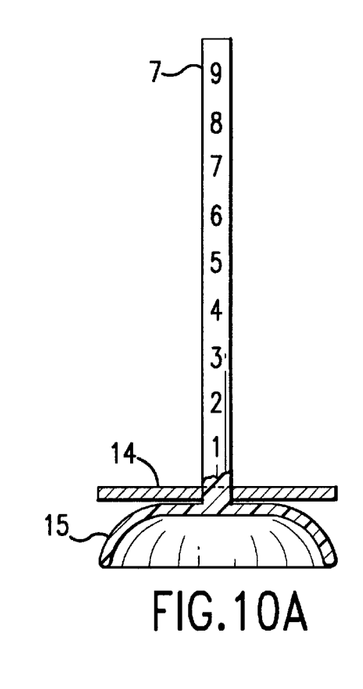
FIG. 10a is an elevational view, partially in section, of an embodiment of gastro-intestinal tube having a dissolvable support bolster according to the present invention, in which the internal bolster is convex, as viewed from a proximal vantage point, and oblong in shape, as viewed from an end.
Figure 10B:
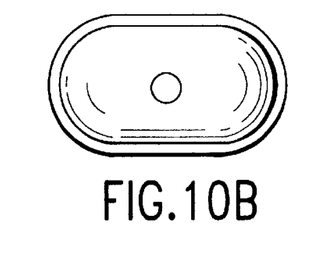

FIG. 9a shows a gastro-intestinal tube of the present invention in which the internal bolster 13 is convex and circular in shape. FIG. 10a shows a gastro-intestinal tube of the present invention in which the internal bolster 11 is proximally convex and oblong in shape (as viewed from an end). FIGS. 9b and 10b show end views of the gastro-intestinal tubes shown in FIGS. 9a and 10a, respectively.

Figure 11A:
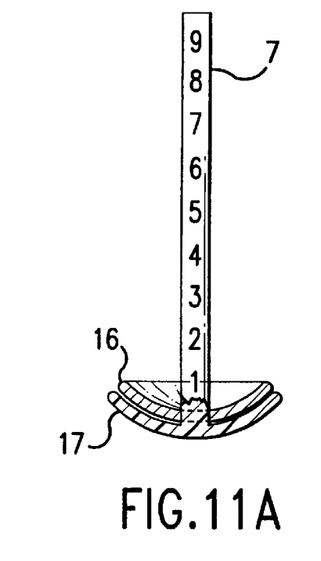
FIG. 11a is an elevational view, partially in section, of an embodiment of gastro-intestinal tube having a dissolvable support bolster according to the present invention, in which both the internal bolster and support bolster are concave, as viewed from a proximal vantage point, and oval in shape, as viewed from an end.
Figure 11B:
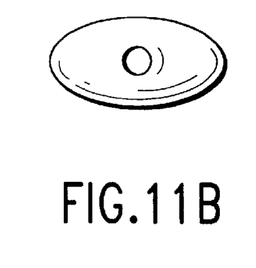
Figure 12A:
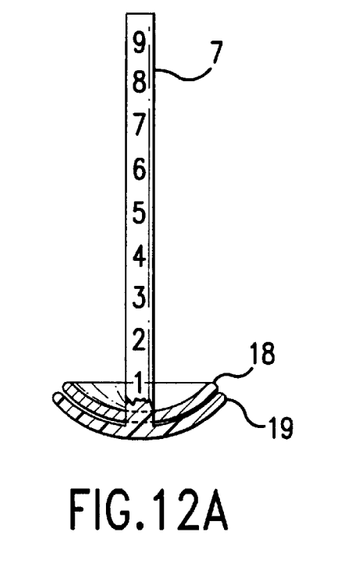
FIG. 12a is an elevational view, partially in section, of an embodiment of gastro-intestinal tube having a dissolvable support bolster according to the present invention, in which both the internal bolster and support bolster are concave, as viewed from a proximal vantage point, and circular in shape, as viewed from an end.
Figure 12B:
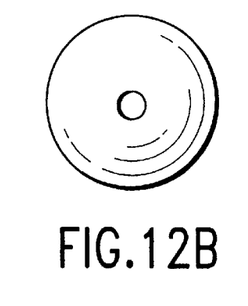
Figure 13A:
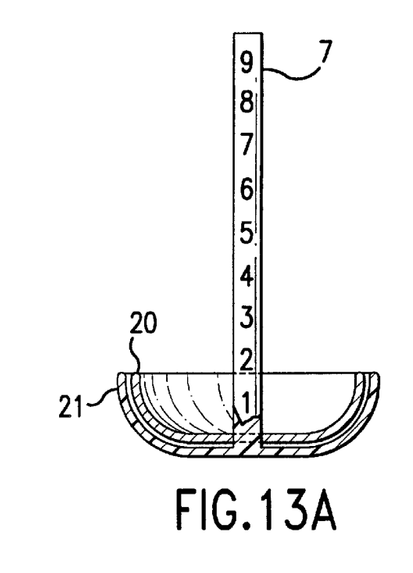
FIG. 13a is an elevational view, partially in section, of an embodiment of gastro-intestinal tube having a dissolvable support bolster according to the present invention, in which both the internal bolster and support bolster are concave, as viewed from a proximal vantage point, and oblong in shape, as viewed from an end.
Figure 13B:
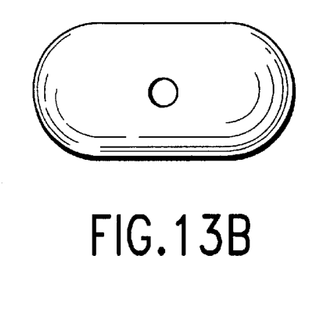

FIG. 11a shows a gastro-intestinal tube of the present invention in which both the internal bolster 17 and support bolster 16 are concave and oval in shape. With this concave shape, the internal bolster 17 is resistant to migration and traction removal. FIG. 12a shows a gastro-intestinal tube of the present invention in which both the internal bolster 19 and support bolster 18 are concave and circular in shape. FIG. 13a shows a gastro-intestinal tube of the present invention in which both the internal bolster 21 and support bolster 20 are concave and oblong in shape. FIGS. 11b, 12b and 13b show end views of the gastro-intestinal tubes shown in FIGS. 11a, 12a, and 13a, respectively.

Figure 14A:
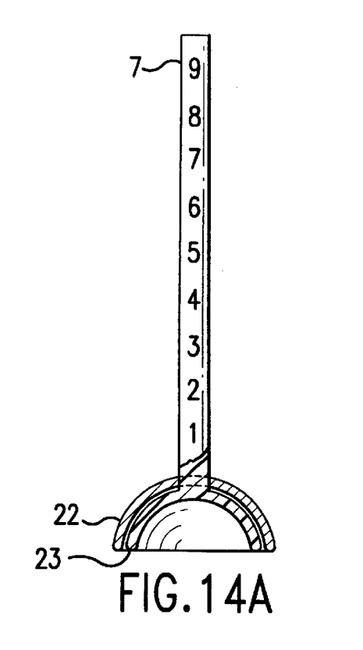
FIG. 14a is an elevational view, partially in section, of an embodiment of gastro-intestinal tube having a dissolvable support bolster according to the present invention, in which both the the internal bolster and support bolster are convex, as viewed from a proximal vantage point, and oval in shape, as viewed from an end.
Figure 14B:
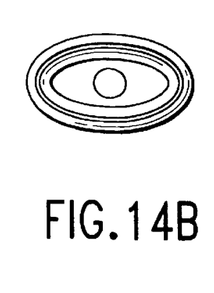
Figure 15A:
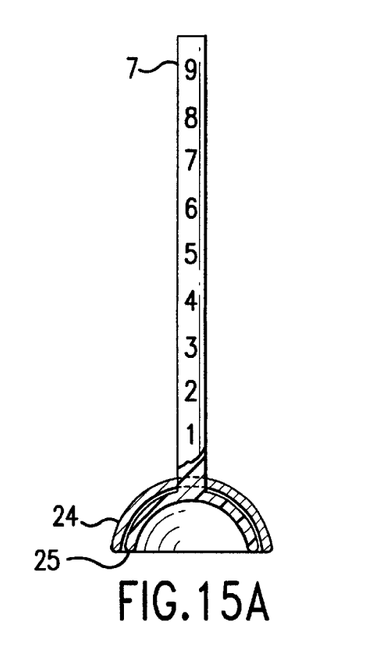
FIG. 15a is an elevational view, partially in section, of an embodiment of gastro-intestinal tube having a dissolvable support bolster according to the present invention, in which both the internal bolster and support bolster are convex, as viewed from a proximal vantage point, and circular in shape, as viewed from an end.
Figure 15B:
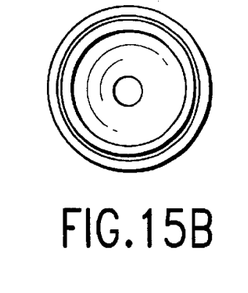
Figure 16A:
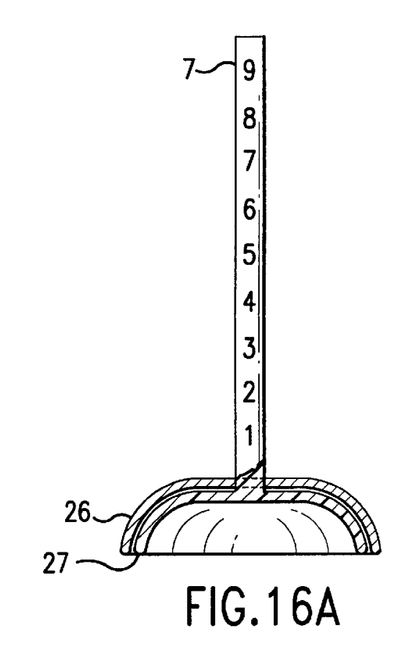
FIG. 16a is an elevational view, partially in section, of an embodiment of gastro-intestinal tube having a dissolvable support bolster according to the present invention, in which both the internal bolster and support bolster are convex, as viewed from a proximal vantage point, and oblong in shape, as viewed from an end.
Figure 16B:
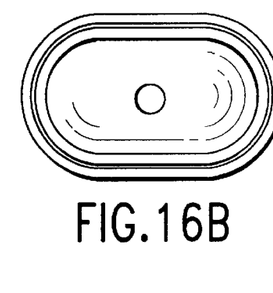

FIG. 14a shows a gastro-intestinal tube of the present invention in which both the internal bolster 23 and support bolster 22 are convex and oval in shape. With this proximally convex shape, the support bolster 22 can remain in greater contact with the gastric wall, and the internal bolster 23 can be removed by traction pull more easily. FIG. 15a shows a gastro-intestinal tube of the present invention in which both the internal bolster 25 and support bolster 24 are convex and circular in shape. FIG. 16a shows a gastro-intestinal tube of the present invention in which both the internal bolster 27 and support bolster 26 are convex and oblong in shape. FIGS. 14b, 15b and 16b show end views of the gastro-intestinal tubes shown in FIGS. 14a, 15a, and 16a, respectively.

Figure 17A:
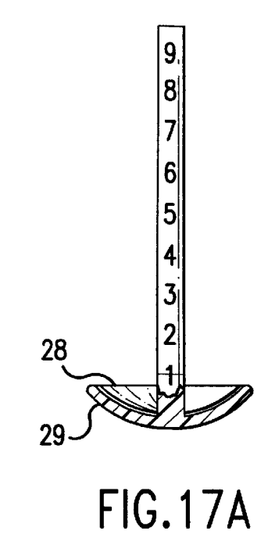
FIG. 17a is an elevational view, partially in section, of an embodiment of gastro-intestinal tube having a dissolvable support bolster according to the present invention, in which the the internal bolster is concave, as viewed from a proximal vantage point, and oval in shape; and the support bolster has a convex distal surface (as viewed from a proximal vantage point) and a substantially planar proximal surface.
Figure 17B:
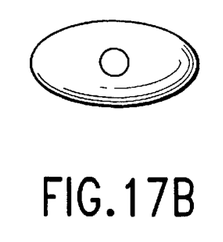
Figure 18A:
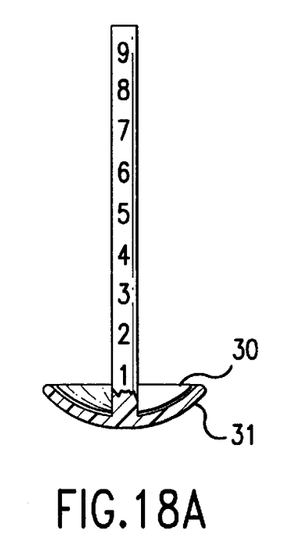
FIG. 18a is an elevational view, partially in section, of an embodiment of gastro-intestinal tube having a dissolvable support bolster according to the present invention, in which the the internal bolster is concave, as viewed from a proximal vantage point, and circular in shape; and the support bolster has a convex distal surface (as viewed from a proximal vantage point) and a substantially planar proximal surface.
Figure 18B:
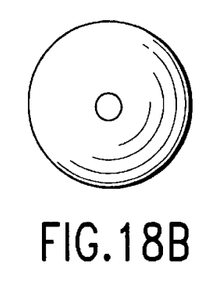
Figure 19A:
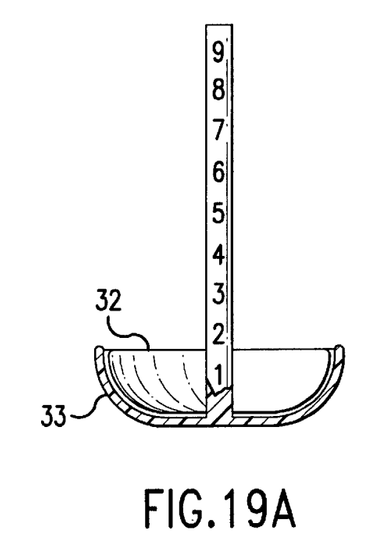
FIG. 19a is an elevational view, partially in section, of an embodiment of gastro-intestinal tube having a dissolvable support bolster according to the present invention, in which the the internal bolster is concave, as viewed from a proximal vantage point, and oblong in shape; and the support bolster has a convex distal surface (as viewed from a proximal vantage point) and a substantially planar proximal surface.
Figure 19B:
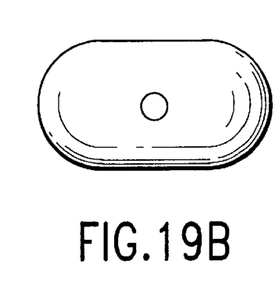

FIG. 17a shows a gastro-intestinal tube of the present invention, in which the internal bolster 29 is concave and oval in shape, and the support bolster 28 has a concave distal surface and a substantially planar proximal surface. FIG. 18a shows a gastro-intestinal tube of the present invention, in which the internal bolster 31 is concave and circular in shape, and the support bolster 30 has a concave distal surface and a substantially planar proximal surface. FIG. 19a shows a gastro-intestinal tube of the present invention, in which the internal bolster 32 is concave and oblong in shape, and the support bolster 33 has a concave distal surface and a substantially planar proximal surface.

What is claimed is:

1. A gastro-intestinal device for being placed within the anatomy comprising:
   a tube having a shaft and proximal and distal ends;
   an internal bolster attached to the distal end of the tube, internal bolster having a collapsible structure which allows removal of the device from within the anatomy; and
   a dissolvable in-vivo internal support bolster which, when the device is properly placed within the anatomy, fits around the tube at the tube's distal end and proximal to the internal bolster, within the anatomy, and which prevents inadvertent removal of the device.

2. A gastro-intestinal device as set forth in claim 1, wherein the support bolster comprises one or more of: a(n) aliphatic polyester, poly(phosphoester), poly(anhydridc), poly(orthoester), poly(phosphazene), polysaccharide, peptide-based polymer, and poly( -ester).

3. A gastro-intestinal device as set forth in claim 1, wherein the support bolster has an outer diameter of approximately 2 cm.

4. A gastro-intestinal device as set forth in claim 1, wherein the support bolster has a dissolution time of between 2 and 4 weeks in vivo.

5. A gastro-intestinal device as set forth in claim 1, wherein the support bolster has a dissolution time of up to 6 months in vivo.

6. A gastro-intestinal device as set forth in claim 1, wherein the support bolster has an external coating comprising an anti-inflammatory agent.

7. A gastro-intestinal device as set forth in claim 1, wherein the support bolster has an external coating comprising an antibiotic agent.

8. A gastro-intestinal device as set forth in claim 1, wherein the support bolster has an external coating comprising an antiviral agent.

9. A gastro-intestinal device as set forth in claim 1, wherein the support bolster has an external coating comprising an antimicrobial agent.

10. A gastro-intestinal device as set forth in claim 1, wherein the support bolster has an external coating comprising an antiencrustation agent.

11. A gastro-intestinal device as set forth in claim 1, wherein the support bolster has an external coating comprising a disinfecting antgent.

12. A gastro-intestinal device as set forth in claim 1, wherein the support bolster has a porous structure capable of holding an anti-inflammatory agent within the pores.

13. A gastro-intestinal device as set forth in claim 1, wherein the support bolster has a porous structure capable of holding an antibiotic agent within the pores.

14. A gastro-intestinal device as set forth in claim 1, wherein the support bolster has a porous structure capable of holding an antiviral agent within the pores.

15. A gastro-intestinal device as set forth in claim 1, wherein the support bolster has a porous structure capable of holding an antimicrobial agent within the pores.

16. A gastro-intestinal device as set forth in claim 1, wherein the support bolster has a porous structure capable of holding an antiencrustation agent within the pores.

17. A gastro-intestinal device as set forth in claim 1, wherein the support bolster has a porous structure capable of holding an disinfecting agent within the pores.

18. A gastro-intestinal device as set forth in claim 1, wherein a portion of the tube shaft, proximally adjacent to the internal bolster is coated with an anti-inflammatory agent.

19. A gastro-intestinal device as set forth in claim 10, wherein the portion of the tube coated with an anti-inflammatory agent has a length of approximately 9 cm.

20. A gastro-intestinal device as set forth in claim 1, wherein a portion of the tube, proximally adjacent to the internal bolster, is coated with an antibiotic drug.

21. A gastro-intestinal device as set forth in claim 20, wherein the portion of the tube coated with an antibiotic drug has a length of approximately 9 cm.

22. A gastro-intestinal device as set forth in claim 1, wherein a medicating agent is incorporated into the support bolster.

23. A gastro-intestinal device as set forth in claim 1, wherein a medicating agent is incorporated into the support bolster and dispensed therefrom.

24. A gastro-intestinal device as set forth in claim 1, wherein a the support bolster has a membrane which limits the rate of dissolution of the support bolster.

25. A gastro-intestinal device as set forth in claim 22, wherein the support bolster has a membrane which limits the rate at which the medicating agent is dispensed.

26. A gastro-intestinal device as set forth in claim 1, wherein the internal bolster is concave, as viewed from a proximal vantage point.

27. A gastro-intestinal device as set forth in claim 1, wherein the internal bolster is convex, as viewed from a proximal vantage point.

28. A gastro-intestinal device as set forth in claim 1, wherein the support bolster is concave, as viewed from a proximal vantage point.

29. A gastro-intestinal device as set forth in claim 1, wherein the support bolster is convex, as viewed from a proximal vantage point.

30. A gastro-intestinal device as set forth in claim 1, wherein the support bolster is shaped as a disk.

31. A gastro-intestinal device as set forth in claim 1, wherein the support bolster has a convex distal surface, as viewed from a proximal vantage point, and a substantially planar proximal surface.

32. A gastro-intestinal device for being placed within the anatomy comprising:
   a tube having a shaft with proximal and distal ends;
   an internal bolster attached to the distal end of the tube, said internal bolster having a collapsible structure which allows traction removal of the tube from within the anatomy; and a biocompatible, dissolvable in-vivo internal support bolster which when the device is properly placed within the anatomy, fits around the tube at the distal end and proximal to the internal bolster within the anatomy, wherein the internal support bolster prevents inadvertent removal of the device, and wherein the internal support bolster is made with one or more of a(n): aliphatic polyester, poly(phosphoester), poly(anhydride), poly(orthoester), poly(phosphazane), polysaccharide, peptide-based polymer, and poly(-ester).

33. A gastro-intestinal device for being placed within the anatomy comprising:

a tube having proximal and distal ends, a tube shaft extending from the proximal end to the distal end;

an internal bolster attached to the distal end of the tube having a collapsible structure which allows traction removal from within the anatomy; and a biocompatible, dissolvable in-vivo internal support bolster which when the device is properly placed within the anatomy, fits around the tube at the distal end and proximal to the internal bolster within the anatomy, wherein the internal support bolster prevents inadvertent removal of the device from the anatomy and is made of biocompatible, dissolvable material, and the internal support bolster further having a coating of medicating agent.

* * * * *